(12) United States Patent
Moreno et al.

(10) Patent No.: US 7,174,205 B2
(45) Date of Patent: Feb. 6, 2007

(54) CARDIAC DIAGNOSTIC SYSTEM AND METHOD

(75) Inventors: Pedro J. Moreno, Cambridge, MA (US); David Goddeau, Watertown, MA (US); Beth T. Logan, Cambridge, MA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 302 days.

(21) Appl. No.: 10/818,527

(22) Filed: Apr. 5, 2004

(65) Prior Publication Data

US 2005/0222508 A1 Oct. 6, 2005

(51) Int. Cl.
*A61B 5/04* (2006.01)
(52) U.S. Cl. .................................... 600/515; 600/523
(58) Field of Classification Search ............... 600/509, 600/515, 523, 525; 128/920, 922; 607/5, 607/30
See application file for complete search history.

(56) References Cited

U.S. PATENT DOCUMENTS

| | | | | |
|---|---|---|---|---|
| 4,523,595 A | * | 6/1985 | Zibell | ................... 607/5 |
| 5,819,007 A | * | 10/1998 | Elghazzawi | ................... 706/46 |
| 6,178,261 B1 | | 1/2001 | Williams et al. | |
| 6,438,410 B2 | * | 8/2002 | Hsu et al. | ................... 600/516 |
| 6,516,219 B1 | * | 2/2003 | Street | ................... 600/515 |
| 2005/0071300 A1 | | 3/2005 | Bartlett et al. | |

FOREIGN PATENT DOCUMENTS

WO      WO 02/091211      11/2002

\* cited by examiner

*Primary Examiner*—Robert E. Pezzuto
*Assistant Examiner*—Tammie K. Heller

(57) ABSTRACT

Computer method and apparatus of analyzing ECG signals of a subject include receiving a subject electrocardiogram signal and comparing it against signal patterns of known cardiac syndromes. A library of example predefined signals is employed. Distance measures indicating similarity of the subject signal to the example predefined signals are produced and form a sequence of vectors. The sequence of vectors are input into a classifier which determines existence of signal patterns indicative of any cardiac syndromes in the subject.

20 Claims, 3 Drawing Sheets

CARDIAC DIAGNOSTIC SYSTEM AND METHOD

BACKGROUND OF THE INVENTION

Over the years cardiologists and electro-cardiologists have developed a body of knowledge pertaining to the analysis of electrocardiogram signals or ECG's. They have identified a number of basic "shapes" that correspond to basic heart syndromes. As of last count, more than 80 basic syndromes can be clearly linked with particular morphologies of the ECG signal (ABC of Clinical Electrocardiography by Francis Morrus, BMJ Publishing Group, 01-2003, ISBN 0727915363) (ECG's by Example, by Jenkings and Gerred, 1997, ISBN 0443058978). These syndromes include ischemic heart disease, hypertrophy patterns, atrioventricular blocks, bundle branch blocks, supraventricular rhythms and ventricular rhythms.

Previous work in analyzing ECG's has focused on building specific detectors for known syndromes. Typically a cardiologist provides a detailed morphological description of what to look for in the signal and this knowledge is encoded in a series of rules that codify an algorithm. This rule-based approach to detection/classification of ECG signals and the potential syndromes they encode has many drawbacks. Among others, clearly this is a time consuming approach that involves a trial and error method of algorithmic design. In addition, the algorithm designer is not exposed to large amounts of data and there is no guarantee that the rules encoding the algorithm are generic enough. Also, extracting the rules from the expert is difficult; sometimes experts don't know exactly how to distinguish one cardiac syndrome from another, they just "know" and cannot explain why they can make the distinction.

Other approaches use ECG data with annotations provided by a cardiologist. The expert assigns labels to regions of the ECG signal indicating whether the signal is normal or if a particular syndrome is present. Then pattern recognition techniques extract features from the ECG signal and using the labels try to build classifiers that minimize the error rate. While this application is better than the previous one and in general does not depend on a detailed understanding of the morphology of the signal (it only requires a label), it fails to take advantage of the extensive knowledge that experts have acquired over the years. Applicants have found that, in effect, too much is demanded from the pattern recognition algorithm that has to extract meaningful features from raw data and figure out on its own the rules that codify a particular syndrome.

SUMMARY OF THE INVENTION

The present invention overcomes the disadvantages of the prior art. In particular, the present invention approach combines the expertise of cardiologists (as encoded in ECG morphologies) with pattern recognition techniques. This effectively combines the best of both worlds, i.e., expert knowledge and automated classification techniques.

In one embodiment, the invention method and apparatus for analyzing ECG signals of a subject include (i) receiving a subject electrocardiogram signal to be analyzed; (ii) using a library of example predefined signals, comparing the subject signal against signal patterns of known cardiac syndromes; (iii) producing distance measures indicating similarity of the subject signal to the example predefined signals; and (iv) forming a sequence of vectors from the produced distance measures. The formed sequence of vectors is used as input into a classifier which determines existence of any cardiac syndromes in the subject (i.e., signal patterns indicative of syndromes).

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

The present invention provides a way of combining the expertise of cardiologists in diagnosing heart disease and syndromes with that of automatic machine learning systems that "learn" based on massive amounts of raw data.

Data-driven pattern classification techniques in which there is a concept of a distance include Support Vector Classifiers, Boosting classifiers and neural networks. At the core of these classification techniques is a distance function called a "kernel" which compares data points, represented as feature vectors, and produces a real number. In the present invention, the data points are segments of an ECG signal which are processed to produce a feature vector. A novel kernel and a collection of labeled training data (both based on cardiologists expertise) are used to learn a set of parameters that characterize the set of classes to be distinguished. This set of parameters, along with the kernel, is then used to classify new data points (ECG signals of unknown conditions).

Figure 1:
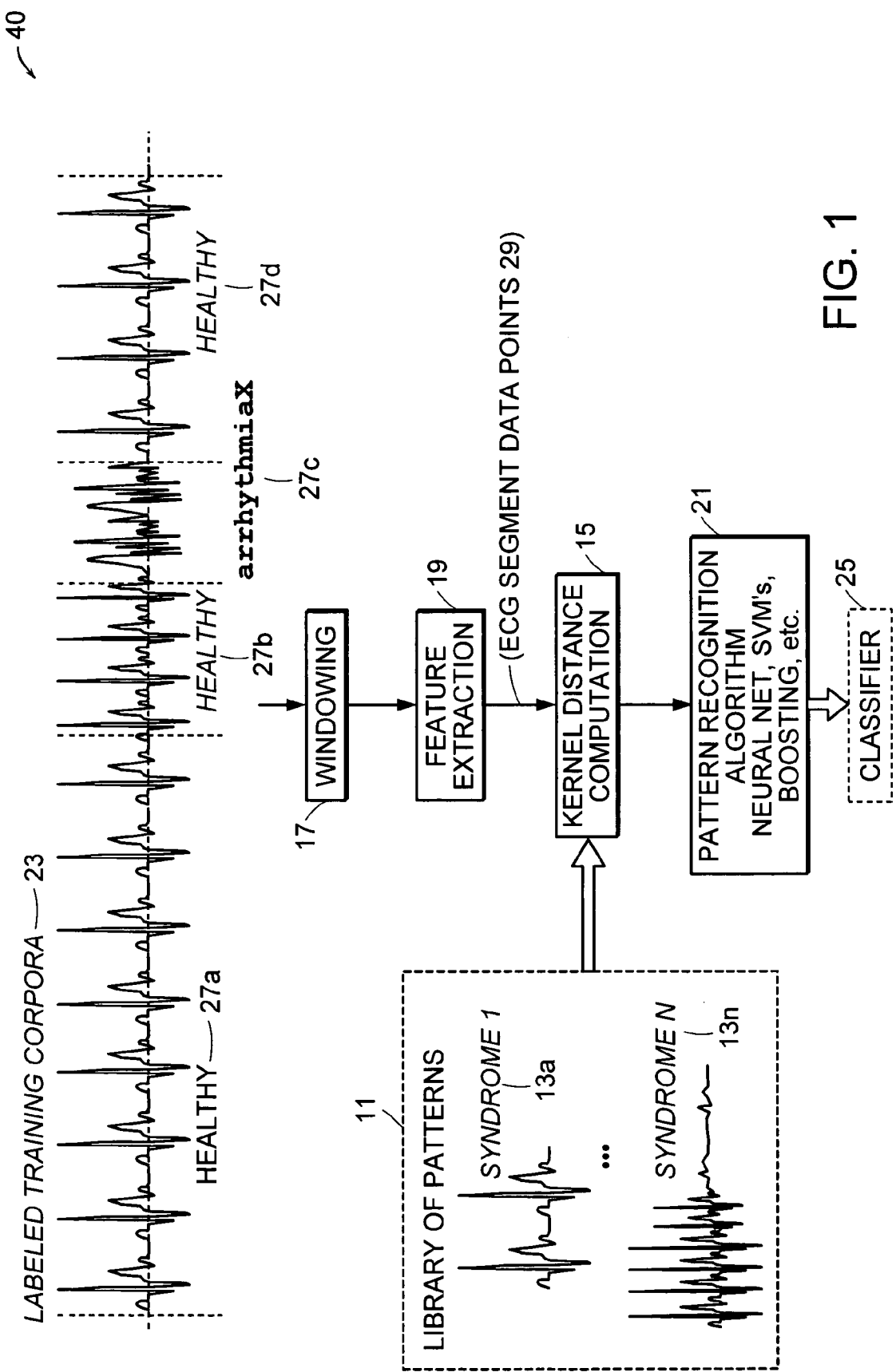
FIG. 1 is a block diagram of a training procedure utilized by the present invention.

The present invention works as follows:

A set of example ECG heartbeat patterns or shapes corresponding to the syndromes to be classified are extracted from the cardiology literature or developed in consultation with cardiologists. Each pattern is normalized in time and amplitude and synchronized with a prototypical heartbeat. The resulting patterns $13a \ldots n$ are considered to be predefined example signals and are stored in a library 11 (implemented through a database, table or other data store) as illustrated in FIG. 1.

Next the patterns 13 of library 11 are used to construct a kernel function 15 that compares two data points and produces a distance. There are many ways this could be done as further detailed below.

The computed distance output by kernel function 15 is input to a pattern recognition engine 21 of a classifier 25. The pattern recognition engine 21 and/or classifier 25 may be a neural network support vector machine or Boosting classifier or other type common in the art. Classifier 25 utilizes the pattern determinations made by pattern recognition engine 21 and determines class of (or otherwise classifies) the subject ECG signal.

In order to train the pattern recognition engine 21 and classifier 25, a labeled or annotated training corpora 23 is employed. Training corpora 23 is a collection of known and previously analyzed ECG signals annotated with corresponding syndrome classes. A windowing member 17 segments each training ECG signal 23 into data chunks 27 typically at changes in signal pattern as illustrated by dotted vertical lies in FIG. 1.

The resulting ECG Signal 23 segments or data chunks 27 are input into a feature extraction module 19. For each segment 27, feature extraction module 19 (i) extracts the signal pattern of interest from the segment/data chunk 27, and (ii) produces ECG segment data points 29 representative of the extracted feature (interesting signal pattern). The feature extraction module 19 outputs these data points 29 for input to kernel function 15.

In one embodiment, in kernel function 15 an internal distance function computes a respective distance between given data points (of an ECG segment) 29 and each of the patterns, 13a . . . n in library 11. To that end, the kernel function 15 computes:

(a) for each pattern 13 (in library 11) a vector of distances from data points 29 in the given ECG segment 27 to data points in the pattern 13 and then computes (b) for each ECG segment 27, the distance between the vectors of (a) using a classical metric (Euclidian distance, Mahalanobis distance, etc.) as its final output.

In another embodiment, kernel function 15 computes a vector of distances for each ECG segment 27 as follows. For a given ECG segment 27, the respective vector has as many components as there are patterns 13 in library 11. That is, each component corresponds to a different pattern 13. Further each component has a similarity value defined as the probability or likelihood of sameness between the data points 29 (of ECG given segment 27) and the data points of the component's associated library pattern 13. From the resulting multi-component vector, kernel function 15 computes and outputs a score for the corresponding ECG segment 27 according to techniques disclosed in U.S. patent application Ser. No. 09/724,269, filed 28 Nov. 2000 herein incorporated by reference. The score represents a measured likeliness (or distance of sorts) between the given ECG segment 27 and the library patterns 13.

Figure 2:
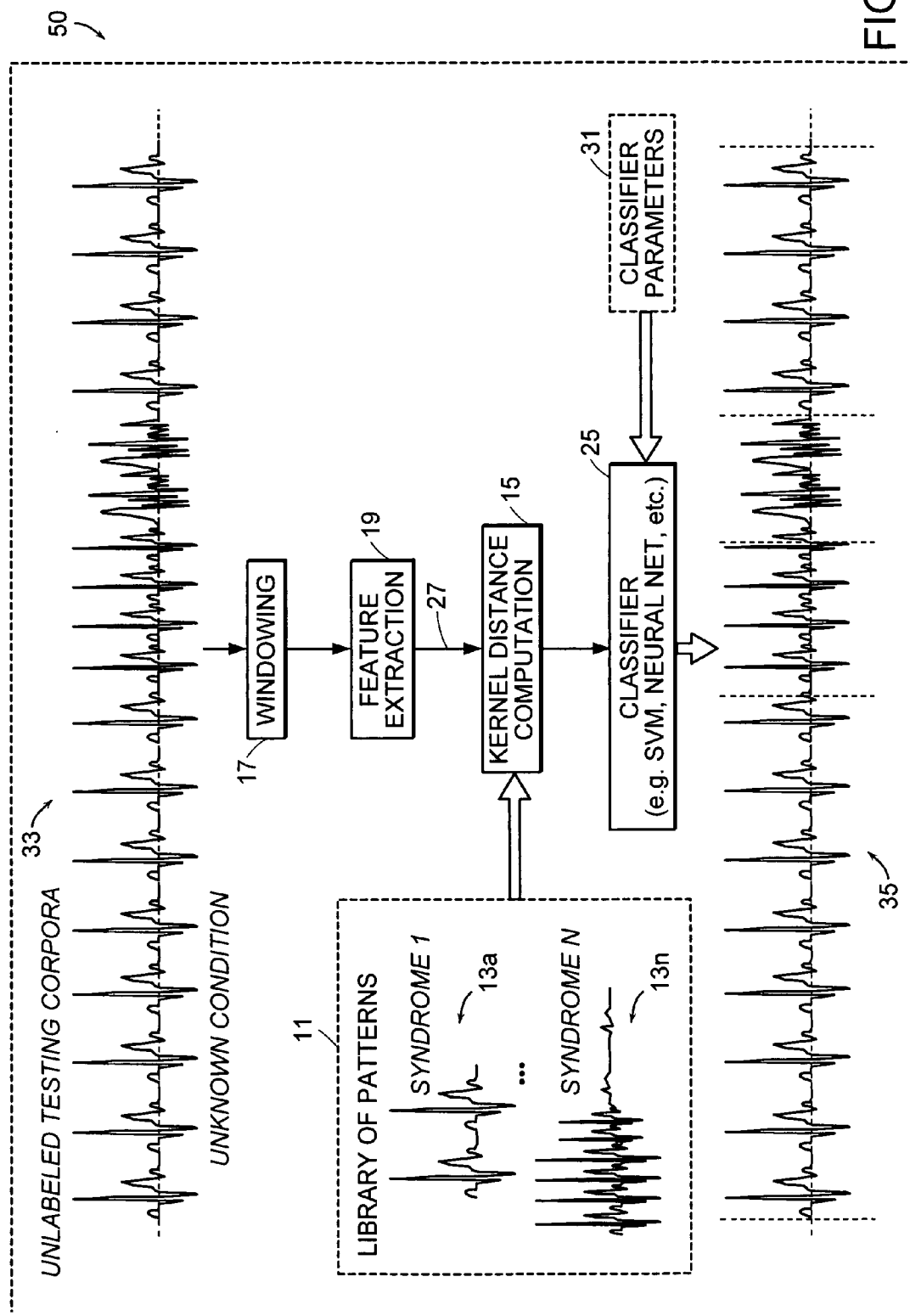
FIG. 2 is a block diagram of ECG signal analysis of the present invention.

The end result of the learning and training of FIG. 1 is a set of parameters 31 (FIG. 2) that further characterize specific conditions for the syndromes being classified. The set of parameters 31 is employed during run time of the present invention as discussed with reference to FIG. 2.

During analysis or testing of ECG signals 33 of a patient (subject) with unknown cardiac conditions, the windowing member 17 and feature extraction module 19 operate as described previously but on test corpora 33. The subject ECG signals 33 (being analyzed) are thus segmented and ultimately represented at the output of feature extraction module 19 as ECG data chunks 27 to being analyzed for indications of possible cardiac syndromes.

The kernel function 15, as constructed according to one of the embodiments or the like described above, receives the subject ECG segments 27 and the library 11 of patterns 13 as input. The kernel function 15 computes distance measures or other quantitative indications of similarity between the subject ECG segments 27 and the library patterns 13. Preferably kernel function 15 produces such a quantitative measure for each subject ECG segment 27 in sequence of the test signal 33. Ultimately from the computed distance measures, kernel function 15 produces a sequence of distance vectors for input to classifier 25. The classifier 25, as trained above in FIG. 1, and supported by learned parameters 31, is responsive to the sequence of distance vectors from kernel function 15 and classifies (or categorizes according to classes) the subject ECG segments 27 of test signal 33. To that end, classifier 25 outputs an annotated version 35 of test signal 33 labeled with specific cardiac syndromes, confidence scores, etc.

In summary, the present invention uses cardiologist-designed kernels 15 based on well known and characterized patterns 13 of cardiac disease as an internal component of a classification algorithm that learns additional parameters 31 from annotated training data 23. The present invention thus incorporates cardiologist expertise in two ways. First in a completely novel way via cardiologist-designed kernels 15, and then in a more traditional way via their annotations on ECG training data 23.

Figure 3:
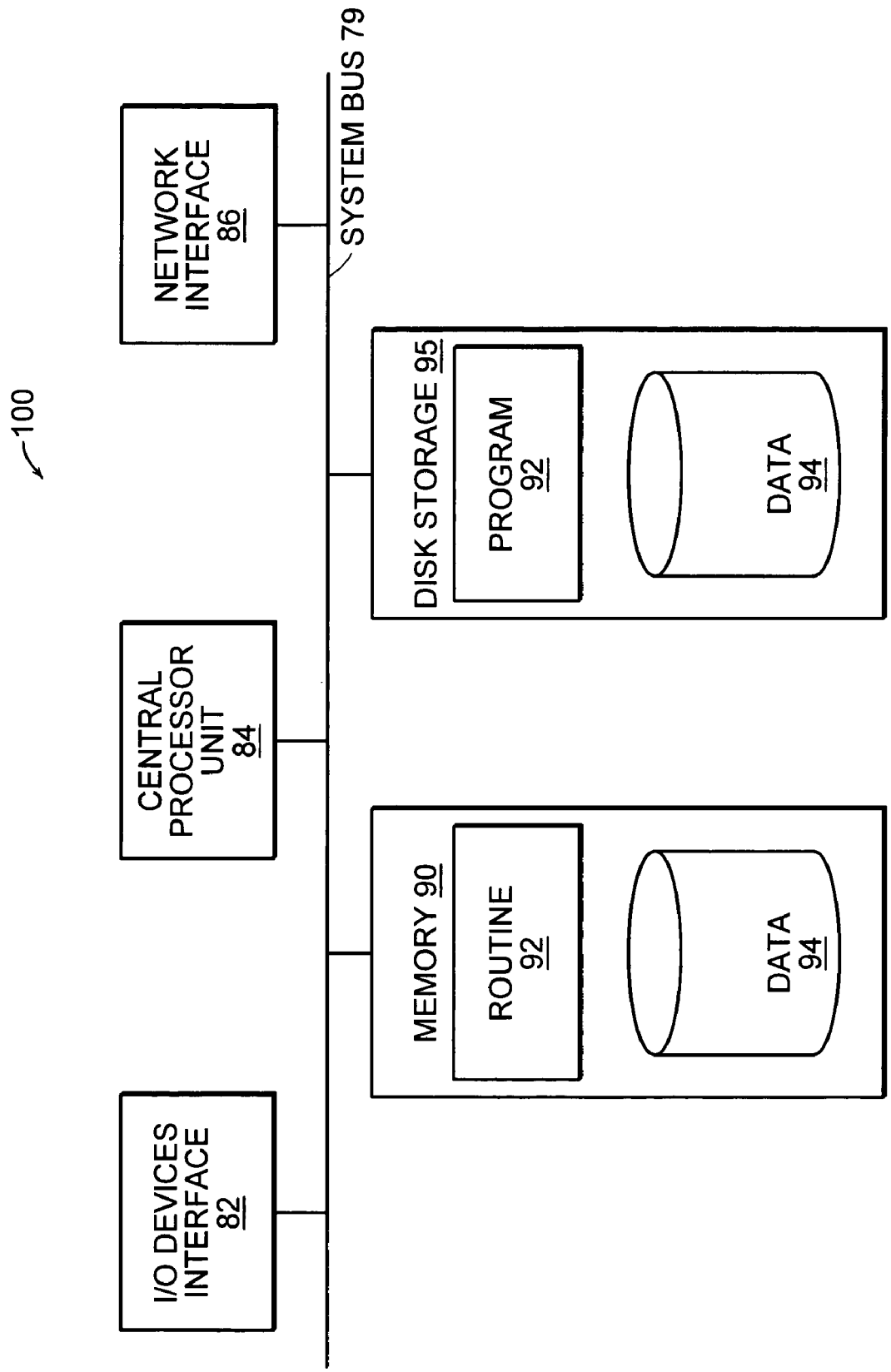
FIG. 3 is a schematic view of a digital processing environment in which the present invention may be practiced.

Illustrated in FIG. 3 is a computer system (environment) 100 in which the present invention may be implemented. That is, training routine/program 40 of FIG. 1 may be executed in such a computer system 100. Testing/analysis routine or program 50 may be executed by the same or a different computer system 100. Each computer system 100 has a working memory 90 for running (executing) routine/programs 40, 50 and is coupled to supporting data stores 94 holding library 11, classifier parameters 31 and the like.

In particular, each computer 100 contains system bus 79, where a bus is a set of hardware lines used for data transfer among the components of a computer. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., displays, printers, speakers, etc.) to the computer. Network interface 86 allows the computer to connect to various other devices attached to a network. Memory 90 provides volatile storage for computer software instructions (e.g., Program Routines 92 and Data 94) used to implement an embodiment of the present invention. Program routines 92 include invention procedures 40, 50 of FIGS. 1 and 2. Disk storage 95 provides non-volatile storage for computer software instructions and data used to implement an embodiment of the present invention. Central processor unit 84 is also attached to system bus 79 and provides for the execution of computer instructions.

Network interface 86 enables procedures 40, 50 to be downloaded or uploaded across a network (e.g., local area network, wide area network or global network). I/O device interface 82 enables procedures 40, 50 to be ported between computers 100 on diskette (CD-ROM, etc.). Other transmission of procedures 40, 50 in whole or in part between computers 100 is in the purview of one skilled in the art. Accordingly, procedures 40, 50 may be run on a standalone computer 100, distributed across computer systems 100, or executed in a client-server fashion or other arrangement.

While this invention has been particularly shown and described with references to preferred embodiments thereof, it will be understood by those skilled in the art that various changes in form and details may be made therein without departing from the scope of the invention encompassed by the appended claims.

For example, the patient may be human or animal.

The invention claimed is:

1. A method of analyzing ECG signals of a subject comprising the computer implemented steps of:

receiving a subject electrocardiogram signal to be analyzed;

using a library of multiple example predefined signals indicative of different known cardiac syndromes, producing respective distance measures indicating similarity of the subject signal to each of the multiple example predefined signals;

forming a sequence of distance vectors from the produced distance measures; and using the sequence of distance vectors as input into a classifier which determines therefrom existence, in the subject, of any one or more of the cardiac syndromes represented in the library, the classifier outputting an annotated version of the subject signal labeled with the determined cardiac syndromes.

2. A method of analyzing as claimed in claim 1, further comprising the step of segmenting the subject signal into working segments;

wherein the step of producing distance measures includes for each working segment, forming a vector with a same number of components as number of example signals in the library, each component corresponding to a different one of the example signals and having a respective distance value indicative of how similar the working segment is to the respective example signal.

3. A method of analyzing as claimed in claim 1, wherein the step of producing distance measures includes:

segmenting the subject signal into a plurality of segments; and for each segment, (a) computing distance between data points of the segment and data points of each example signal of the library such that a vector of distances is formed for each example signal, and (b) defining a distance measure for the segment as a function of distance between the formed vectors of distances.

4. A method of analyzing as claimed in claim 1, further comprising the step of:

labeling segments of an example signal in the library based on output of the classifier.

5. A method of analyzing as claimed in claim 1, wherein the library of example predefined signals holds samples designed by cardiologists, each sample having a respective cardio syndrome and a corresponding example cardiogram signal.

6. A computer apparatus for analyzing ECG signals of a subject comprising:

a module for receiving a subject electrocardiogram signal to be analyzed;

a library of multiple example predefined signals indicative of different known cardiac syndromes;

a kernel function member coupled between the library and the receiving module, the kernel function member (i) producing respective distance measures indicating similarity of the subject signal to each of the example predefined signals, and (ii) forming a sequence of distance vectors from the produced distance measures; and a classifier using the formed sequence of distance vectors as input and determining existence of any one or more of the different known cardiac syndromes in the subject, the classifier outputting an annotated version of the subject signal labeled with the determined cardiac syndromes.

7. The computer apparatus as claimed in claim 6 wherein the receiving module segments the subject signal into working segments; and the kernel function member produces a distance measure for each working segment by forming a vector with a same number of components as number of example signals in the library, each component corresponding to a different one of the example signals and having a respective distance value indicative of how similar the working segment is to the respective example signal.

8. The computer apparatus as claimed in claim 6 wherein the receiving module segments the subject signal into working segments; and the kernel function member for each working segment, (a) computes distance between data points of the segment and data points of each example signal of the library such that a vector of distances is formed for each example signal, and (b) defines a distance measure for the working segment as a function of distance between the formed vectors of distances.

9. The computer apparatus as claimed in claim 6 wherein segments of the example signals in the library are labeled based on output of the classifier.

10. The computer apparatus as claimed in claim 6, wherein the library of example signals holds samples defined by cardiologists, each sample having a respective cardiac syndrome and a corresponding example cardiogram signal.

11. A computer apparatus for analyzing ECG signals of a subject comprising:

means for receiving a subject ECG signal;

library means for storing multiple example predefined signals indicative of different known cardiac syndromes;

kernel function means responsive to the subject ECG signal for (i) producing distance measures indicating similarity of the subject signal to the example predefined signals and (ii) forming a sequence of distance vectors from the produced distance measures; and classifying means for using the formed sequence of distance vectors as input and determining existence of any one of the different known cardiac syndromes in the subject. The classifying means outputting the subject signal annotated with indications of the determined cardiac syndromes.

12. The computer apparatus as claimed in claim 11 wherein the means for receiving includes means for segmenting the subject signal into working segments.

13. The computer apparatus as claimed in claim 12 wherein the kernel function means produces a distance measure for each working segment by forming a vector with a same number of components as number of example signals in the library, each component corresponding to a different one of the example signals and having a respective distance value indicative of how similar the working segment is to the respective example signal.

14. The computer apparatus as claimed in claim 12 wherein the kernel function means for each working segment (a) computes distance between data points of the segment and data points of each example signal of the library such that a vector of distances is formed for each example signal, and (b) defines a distance measure for the working segment as a function of distance between the formed vectors of distances.

15. The computer apparatus as claimed in claim 11 wherein segments of the example signals in the library are labeled based on output of the classifying means.

16. The computer apparatus as claimed in claim 11 wherein the library means holds examples defined by cardiologists, each example having a respective cardiac syndrome and a corresponding example cardiogram signal.

17. A system for analyzing ECG signals of a subject comprising:

library means for providing multiple example predefined signals indicative of different known cardiac syndromes;

measuring means for producing distance measures indicating similarity of a subject signal to the example predefined signals;

vector means for forming a sequence of distance vectors from the produced distance measures for use of the sequence of distance vectors as input into a classifier which determines therefrom existence of any one of the known cardiac syndromes in the subject, the classifier outputting an annotated version of the subject signal labeled with the determined cardiac syndromes.

18. A system as claimed in claim 17 further comprising segmenting means for segmenting the subject signal into working segments;

wherein the measuring means for each working segment forms a vector with a same number of components as number of example signals in the library means, each component corresponding to a different one of the example signals and having a respective distance value indicative of how similar the working segment is to the respective example signal.

19. A system as claimed in claim 17 wherein the measuring means segments the subject signal into a plurality of segments; and for each segment, (a) computes distance between data points of the segment and data points of each example signal of the library means such that a vector of distances is formed for each example signal, and (b) defines a distance measure for the segment as a function of distance between the formed vectors of distances.

20. A system as claimed in claim 17 further comprising labeling means for labeling segments of an example signal in the library means based on output of the classifier.

* * * * *

UNITED STATES PATENT AND TRADEMARK OFFICE
CERTIFICATE OF CORRECTION

PATENT NO. : 7,174,205 B2 Page 1 of 1
APPLICATION NO. : 10/818527
DATED : February 6, 2007
INVENTOR(S) : Pedro J. Moreno et al.

It is certified that error appears in the above-identified patent and that said Letters Patent is hereby corrected as shown below:

In column 6, line 37, in Claim 11, delete "subject. The" and insert -- subject, the --, therefor.

Signed and Sealed this

Fifth Day of May, 2009

JOHN DOLL
*Acting Director of the United States Patent and Trademark Office*